(12) United States Patent
Liu et al.

(10) Patent No.: US 8,722,918 B2
(45) Date of Patent: May 13, 2014

(54) PROCESS FOR PRODUCING CL-C4 ALKYL NITRITE

(75) Inventors: Juntao Liu, Shanghai (CN); Siqin Li, Shanghai (CN); Lei Li, Shanghai (CN); Linna Zhang, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 370 days.

(21) Appl. No.: 13/088,253

(22) Filed: Apr. 15, 2011

(65) Prior Publication Data

US 2011/0257425 A1     Oct. 20, 2011

(30) Foreign Application Priority Data

Apr. 15, 2010   (CN) .......................... 2010 1 0146997
Feb. 25, 2011   (CN) .......................... 2011 1 0045615

(51) Int. Cl.
*C07C 201/04* (2006.01)

(52) U.S. Cl.
CPC ................................. *C07C 201/04* (2013.01)
USPC ......................................................... 558/488

(58) Field of Classification Search
CPC ................................................... C07C 201/04
USPC ......................................................... 558/488
See application file for complete search history.

(56) References Cited

FOREIGN PATENT DOCUMENTS

| CN | 1064338 | 9/1992 |
| CN | 1116146 | 2/1996 |
| CN | 1148589 | 4/1997 |
| CN | 1895766 | 1/2007 |
| CN | 101143821 | 3/2008 |
| CN | 201770631 U | * 3/2011 |
| EP | 0 023 745 | 2/1981 |

OTHER PUBLICATIONS

Wang et al. Chemical Engineering Journal 2010, 163, 422-428.*
Machine translation of CN 201770631 U, obtained May 15, 2013 from http://cs.dialog.com/client/csc_sh127/.*

* cited by examiner

*Primary Examiner* — Joseph Kosack
*Assistant Examiner* — Matthew Coughlin
(74) *Attorney, Agent, or Firm* — Novick, Kim & Lee, PLLC; Allen Xue

(57) ABSTRACT

The present invention relates to a process for producing $C_1$-$C_4$ alkyl nitrite, comprising loading a resin catalyst layer and/or a porous filler layer into a reactor, passing nitrogen oxide, oxygen and $C_1$-$C_4$ alkanol as raw materials through the resin catalyst layer and/or porous filler layer in a counter current, parallel current or cross current manner, reacting under the conditions including a reaction temperature of from 0 to 150° C., a reaction pressure of from –0.09 to 1.5 MPa, a molar ratio of $C_1$-$C_4$ alkanol/nitrogen oxide of 1-100:1, a molar ratio of nitrogen oxide/oxygen of 4-50:1, to obtain an effluent containing $C_1$-$C_4$ alkyl nitrite, wherein said nitrogen oxide is NO, or a mixed gas containing NO and one or more selected from $N_2O_3$ and $NO_2$.

19 Claims, No Drawings

PROCESS FOR PRODUCING C1-C4 ALKYL NITRITE

FIELD OF THE INVENTION

The present invention relates to a process for producing $C_1$-$C_4$ alkyl nitrite, in particular a process for producing $C_1$-$C_4$ alkyl nitrite useful in the production of oxalate by CO coupling.

BACKGROUND OF THE INVENTION

Oxalate is an important organic chemical material, and widely used in fine chemicals for the production of various dyes, medicines, important solvents, extractants and intermediates. In 21$^{st}$ century, oxalate as a degradable environmental-protection-type engineering plastic monomer is internationally and widely recognized. In addition, hydrolysis of oxalate at normal pressure can produce oxalic acid, and aminolysis of oxalate at normal pressure can produce high grade sustained-release fertilizer—oxamide. Oxalate can also be used as solvent for production of medicines, dye intermediates and the like. For example, various condensation reactions can be carried out by using oxalate together with fatty acid esters, cyclohexylacetophenone, amino alcohols and many heterocyclic compounds. Oxalate can also be used for synthesizing thymine as hormone in the medicine. Low pressure hydrogenation of oxalate can be used for producing ethylene glycol which is a very important chemical raw material. Currently, ethylene glycol is heavily dependent on production via the petroleum routine and has a higher cost. China imports a lot of ethylene glycol each year, and the import volume in 2007 was close to 4,800,000 tons. The conventional process for production of oxalate involves preparing by esterification of oxalic acid with alcohols, which has a high production process cost, high energy consumption, heavy pollution and unreasonable utilization of raw materials. People are seeking for a low cost and an environment-friendly process route. In the 1960s, D. F. Fenton of Integrated Oil Company, U.S.A. found that dialkyl oxalate could be directly synthesized from CO, alcohols and oxygen by oxidization-carbonylation. From then on, UBE Industries Ltd., Japan and ARCO, U.S.A. successively carried on studies and developments in such field.

As seen from the development course, the synthesis of oxalate by the CO oxidization-coupling method can be divided into the liquid phase method and the gaseous phase method. The synthesis of oxalate by the CO liquid phase method requires more stringent conditions: the reaction is conducted at high pressure; the apparatus is easily corroded by the liquid phase system; and the catalyst is easy to lose during the reaction. The gaseous phase method for producing oxalate by CO coupling is advantageous. Sequentially, UBE Industries Ltd., Japan and Montedison S.P.A, Italy have also developed studies on the gaseous phase method in 1978, wherein the process for synthesizing oxalate by gaseous catalysis developed by UBE Industries Ltd. is conducted at a pressure of 0.5 MPa and a temperature of 80-150° C.

The reaction procedures for synthesizing oxalate are as follows.

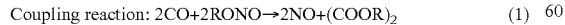

Coupling reaction: $2CO+2RONO \rightarrow 2NO+(COOR)_2$  (1)

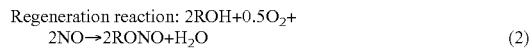

Regeneration reaction: $2ROH+0.5O_2+2NO \rightarrow 2RONO+H_2O$  (2)

According to the procedures above, it can be seen that the technical key of such system lies in reasonably utilizing NO, RONO, ROH in said two-step reaction procedures in high selectivity and high efficiency.

However, the truth is that, except for the primary product-alkyl nitrites, side reactions, in particular production of side product-nitric acid, often occur in the reaction procedure of step (2), which necessarily consumes more NO gas, increases energy consumption and cost and erodes the apparatus at the same time. Although there are many documents regarding how to produce alkyl nitrites, there is less report on how to effectively increase selectivity of alkyl nitrites, and to prevent in a better way the side reaction of nitric acid from occurrence.

CN200710060003.4 discloses a process for preparing diethyl oxalate by CO coupling, comprising using the gaseous phase method, coupling CO by catalyzing with a bi-metal supported-type catalyst in the presence of ethyl nitrite to produce a crude product of diethyl oxalate. The reaction is a self-sealing circulation process. CO gas is mixed with ethyl nitrite from the regeneration reactor, preheated and fed into a coupling reactor. After reaction, the gas is condensed and separated to obtain a colorless, transparent condensate of diethyl oxalate. Uncondensed gas containing NO is re-fed into the regeneration reactor to react with ethanol and oxygen and to produce ethyl nitrite, and the resultant ethyl nitrite is recycled to the coupling reactor for continuous use. The selectivity of ethyl nitrite is not mentioned in the invention.

CN 95116136.9 discloses a catalyst for synthesizing oxalate, wherein Zr is used as an auxiliary agent for developing a novel Pd—Zr/$Al_2O_3$ catalyst by the immersion method. Such catalyst is used for synthesizing oxalate from CO and nitrite via gaseous phase catalysis in a fixed bed reaction apparatus. Likewise, such patent document does not involve the selectivity of nitrites and the inhibition against the side reaction of nitric acid.

Resin catalyst is a polymer material containing active groups, having the synthesis functions and formed by incorporating ion exchange groups having different properties from crosslinked macromolecular copolymers. Resin catalysts have been widely applied in many fields at present, e.g. water purification, decolorization of chemicals, catalytic reaction, such as hydrogenation, isomerization reaction of olefins and the like. However, there is no report on applying a resin catalyst in the alkylation of alkyl nitrites.

Additionally, there is no report on applying a porous filler layer in the alkylation of alkyl nitrites.

Imperial Chemical Industries Ltd, ICI, proposed the patent application EP0023745 A3. Such patent mentions that a rotating bed can be used for the processes such as absorption, desorption, distillation and the like, but does not disclose any applied technique in an industrial scale. CN1064338A discloses a process for water injection and deoxidation of oil field using a rotating bed. CN1116146A discloses a process for producing ultrafine particles under high gravity field.

High-gravity technology appeared in early 1980s. The internal mechanism thereof is still continuing to be explored; studies on the application and development thereof are constantly in progress; and new application fields are still be developed unceasingly. For the moment, there is no report on the application of a rotating bed in the production of $C_1$-$C_4$ alkyl nitrites.

CONTENTS OF THE INVENTION

The technical problem to be solved by the present invention is the low selectivity of $C_1$-$C_4$ alkyl nitrite in the prior documents, and to provide a novel process for producing $C_1$-$C_4$ alkyl nitrite, wherein such process has the advantage of high selectivity of $C_1$-$C_4$ alkyl nitrite.

In order to solve the technical problem above, the technical solution used in the present invention is as follows: a process for produce $C_1$-$C_4$ alkyl nitrite, comprising loading a resin catalyst layer and/or a porous filler layer into a reactor, passing nitrogen oxide, oxygen and $C_1$-$C_4$ alkanol as raw materials through the resin catalyst layer and/or porous filler layer in a counter current, parallel current or cross current manner, reacting under the conditions including a reaction temperature of from 0 to 150° C., a reaction pressure of from −0.09 to 1.5 MPa, a molar ratio of $C_1$-$C_4$ alkanol/nitrogen oxide of 1-100:1, a molar ratio of nitrogen oxide/oxygen of 4-50:1, to obtain an effluent containing $C_1$-$C_4$ alkyl nitrite, wherein said nitrogen oxide is NO, or a mixed gas containing NO and one or more selected from $N_2O_3$ and $NO_2$. When a porous filler layer is used in the reactor, such reactor is preferably a rotating high-gravity reactor.

In one preferred embodiment, the reactor is a rotating high-gravity reactor, wherein a porous filler layer is fixed onto the rotor of the rotating high-gravity reactor. In another preferred embodiment, a resin catalyst is further fixed onto the rotor of the rotating high-gravity reactor.

In one preferred embodiment, a resin catalyst is loaded into the reactor, wherein the resin catalyst is preferably an acidic ion exchange resin catalyst.

In one preferred embodiment, the porous filler layer is, for example, an inert filler web, a porous web, a stent or a porous plate (e.g. stainless steel, corrosion resistant polymeric materials).

In one preferred embodiment, the molar number of NO in said nitrogen oxide is greater than that of $NO_2$, if any, in said nitrogen oxide.

In one preferred embodiment, the reaction temperature ranges from 10 to 100° C., more preferably from 10 to 60° C.; the reaction pressure ranges from −0.05 to 1.0 MPa, more preferably from −0.05 to 0.8 MPa; the molar ratio of $C_1$-$C_4$ alkanol to nitrogen oxide is 1-50:1, more preferably 1-20:1; and the molar ratio of nitrogen oxide to oxygen is 4-20:1, more preferably 4-10:1.

In one preferred embodiment, the rotor in the rotating high-gravity reactor has a rotating speed of from 100 to 5,000 rpm, more preferably from 300 to 3,000 rpm.

In one preferred embodiment, $C_1$-$C_4$ alkanol is selected from the group consisting of methanol, ethanol and n-propanol, more preferably methanol or ethanol.

Resin catalyst is a polymer material containing active groups, having the synthesis functions and formed by incorporating ion exchange groups having different properties from crosslinked macromolecular copolymers. Resin catalysts have been widely applied in many fields at present, e.g. water purification, decolorization of chemicals, catalytic reaction, such as hydrogenation, isomerization reaction of olefins and the like.

It is well known that all the substances on earth are attracted by the earth due to the force of gravity. High-gravity field is an environment having a strength much greater than that of the gravity field of the earth. The force suffered by the substances in the high-gravity field is called high-gravity, and the practical technology produced by utilizing the scientific principle of high-gravity is called high-gravity technology.

High-gravity technology is the new technology strengthening the multiphase flow transmission and reaction process, and widely recognized at home and abroad, and has a widely commercial application prospect in the industrial fields of environmental protection and material biological chemistry since it came out in the last century. However, high-gravity technology is at an application-developing stage at present, which is embodied in the high-gravity gas-solid fluidized technology and high-gravity gas-liquid mass transfer technology.

In the high-gravity environment which is hundreds of to thousands of times the gravity field of the earth, great shearing force tears liquid into liquid membrane, liquid filament and liquid drop in a micrometer or nanometer scale and produces giant and quickly updated phase interfaces, which extremely increases the gas-liquid-contact specific surface area, enhances the interphase mass transfer rate by 1-3 orders of magnitude than that in the conventional column apparatus and extremely strengthens the microscopic mixing and mass transfer processes. The production efficiency per unit device volume is thus increased by 1 to 2 orders of magnitude.

As an apparatus for producing high-gravity field, the rotating high-gravity reactor usually consists of gas and liquid inlet pipes, rotor, and gas and liquid outlets, and generally has a porous filler layer. The operating principle thereof is that the gas phase is tangentially introduced into the outer cavity of the rotor via the gas inlet pipe, and fed into the filler from the outer edge of the rotor under the gas action. Liquid is fed into the inner cavity of the rotor via the liquid inlet pipe, and sprayed onto the inner edge of the rotor via sprayer. Under the action of the filler (or catalyst) in the rotor, liquid fed into the rotor has an increasing axial speed and is pushed to the outer edge of the rotor by the resultant centrifugal force. During such process, liquid is dispersed by the filler (or catalyst) and breaks into pieces to form the extremely great and continuously updated surface area, wherein the tortuous flow passages exacerbate the updating of the liquid surfaces. In this way, extremely better mass transfer and reaction conditions are formed inside the rotor. Liquid is thrown to the shell by the rotor, collected and removed from the high-gravity machine via the liquid outlet pipe. Gas leaves the rotor from the center of the rotor, and is drawn out via the gas outlet pipe, so as to finish the mass transfer and reaction processes.

Studies show that, during the oxidation-alkylation of nitrogen oxide with oxygen and alcohols to form alkyl nitrites, the reactions conditions, including reaction temperature, reaction pressure, residence time, manner for mixing nitrogen oxide, oxygen and alcohols and the like, all have significant effects on the selectivity of nitrites. In particular, the occurrence of the side reaction of nitric acid formation is closely related to the reaction of the formation of $N_2O_4$ from nitrogen oxide in the raw materials, and thus the technical key is to prevent the formation of $N_2O_4$. Studies also find that the oxidization-alkylation reaction of nitrogen oxide with oxygen and alcohols to produce alkyl nitrites is a quick reaction, while the side reactions of nitric acid formation and the like is lower. The reaction rate of the NO oxidization-alkylation reaction is primarily affected by the gas-liquid mass transfer resistance. If the gas-liquid mass transfer efficiency is effectively improved, the probability of producing $N_2O_4$ can be effectively reduced, so as to further prevent the side reactions such as nitric acid formation and the like from occurrence. On the basis of sufficient studies on the features of the oxidization-alkylation reaction of nitrogen oxide with oxygen and alcohols, the technical solution of the present invention further puts forward a highly reactive resin catalyst and/or a porous filler layer to increase the selectivity. In one preferred embodiment, a rotating high-gravity reactor is used as the reactor, wherein the porous filler layer is fixed onto the rotor of the rotating high-gravity reactor. In another more preferred embodiment, the rotor having the porous filler layer in the rotating high-gravity reactor also has said highly reactive resin catalyst, thus greatly increasing the gas-liquid mass transfer rate by a geometric order of magnitude, more effectively promoting the primary reaction and inhibiting the occurrence of side reactions, so as to increase the coefficient of utilization of the raw materials such as NO and the like and to greatly increase the selectivity of nitrites.

According to one preferred technical solution of the present invention, nitrogen oxide, oxygen and $C_1$-$C_4$ alkanol as raw materials contact and react in the rotating high-gravity reactor under the conditions including a reaction temperature of from 10 to 60° C., a reaction pressure of from −0.05 to 0.8 MPa, a molar ratio of $C_1$-$C_4$ alkanol to nitrogen oxide of 1-20:1, a molar ratio of nitrogen oxide to oxygen of 4-10:1, and a rotating speed of the rotor in the rotating high-gravity reactor of from 300 to 3,000 rpm, to produce an effluent containing $C_1$-$C_4$ alkyl nitrite, and the resulting selectivity of $C_1$-$C_4$ alkyl nitrite may be greater than 99%.

Unless otherwise defined, all technical and scientific terms used herein have the same meaning as commonly understood by one of ordinary skill in the art to which the present invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "comprising" means that other steps and ingredients that do not affect the final result can be added. This term encompasses the terms "consisting of" and "consisting essentially of".

Throughout this disclosure, various aspects of the present invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 (1-6) should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Except in the operating (working) and comparative examples, or where otherwise explicitly indicated, all numbers in this Description indicating amounts of material or conditions of reaction, physical properties of materials and/or use are to be understood as modified by the word "about". Whenever a numerical range is indicated herein, it is meant to include any cited numeral (fractional or integral) within the indicated range. The phrases "between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the singular form "a", "an", and "the" include plural references unless the context clearly dictates otherwise.

The present invention is further elaborated by the following examples, but is not limited to them.

EMBODIMENTS

Example 1

Nitrogen oxide, oxygen and methanol were fed in a parallel current manner into the (having the model of HIGEE100 and manufactured by Shanghai Research Institute of Petrochemical Technology, wherein a porous metal plate is fixed onto the rotor). Nitrogen oxide was the mixture of NO and $NO_2$ in a molar ratio of 2:1, and the molar ratio of NO to oxygen was 10:1. Under the conditions including a reaction temperature of 40° C., a reaction pressure of 0.2 MPa, a methanol/NO molar ratio of 1.5:1, and a rotating speed of the rotor in the rotating high-gravity reactor of 1,000 rpm, the raw materials were contacted and reacted in the rotating high-gravity reactor, and the results showed that the selectivity of methyl nitrite was 99.67%.

Example 2

Nitrogen oxide, oxygen and methanol were fed in a counter current manner into the high-gravity reactor which was the same as the rotating high-gravity reactor in Example 1 of the patent publication CN1895766A wherein a fixed stent and a porous wire web were fixed on the rotor (the same reactor was also employed in the following Examples 3-12). Nitrogen oxide was NO, and the molar ratio of NO to oxygen was 6:1. Under the conditions including a reaction temperature of 10° C., a reaction pressure of −0.08 MPa, a methanol/NO molar ratio of 2:1, and a rotating speed of the rotor in the rotating high-gravity reactor of 500 rpm, the raw materials were contacted and reacted in the rotating high-gravity reactor, and the results showed that the conversion rate of oxygen was 100%, and the selectivity of methyl nitrite was 99.25%.

Example 3

002CR type resin catalyst (Jiangsu Suqing Water Treatment Engineering Group Co., Ltd.) labelled as Suqing brand was loaded into the high-gravity reactor. Nitrogen oxide, oxygen and methanol were fed in a counter current manner into the rotating high-gravity reactor. Nitrogen oxide was NO, and the molar ratio of NO to oxygen was 5:1. Under the conditions including a reaction temperature of 30° C., a reaction pressure of −0.05 MPa, a methanol/NO molar ratio of 1.5:1, and a rotating speed of the rotor in the rotating high-gravity reactor of 1,200 rpm, the raw materials were contacted and reacted in the rotating high-gravity reactor, and the results showed that the selectivity of methyl nitrite was 99.71%.

Example 4

Nitrogen oxide, oxygen and methanol were fed in a counter current manner into the rotating high-gravity reactor. Nitrogen oxide was NO, and the molar ratio of NO to oxygen was 8:1. Under the conditions including a reaction temperature of 50° C., a reaction pressure of −0.02 MPa, a methanol/NO molar ratio of 20:1, and a rotating speed of the rotor in the rotating high-gravity reactor of 3,000 rpm, the raw materials were contacted and reacted in the rotating high-gravity reactor, and the results showed that the selectivity of methyl nitrite was 99.43%.

Example 5

005CR type resin catalyst (Jiangsu Suqing Water Treatment Engineering Group Co., Ltd.) labelled as Suqing brand was loaded into the high-gravity reactor. Nitrogen oxide, oxygen and butanol were fed in a parallel manner into the rotating high-gravity reactor. Nitrogen oxide was NO, and the molar ratio of NO to oxygen was 20:1. Under the conditions including a reaction temperature of 30° C., a reaction pressure of 0.2 MPa, a butanol/NO molar ratio of 5:1, and a rotating speed of the rotor in the rotating high-gravity reactor of 1,500 rpm, the raw materials were contacted and reacted in the rotating high-gravity reactor, and the results showed that the selectivity of butyl nitrite was 99.88%.

Example 6

Nitrogen oxide, oxygen and butanol were fed in a parallel current manner into the rotating high-gravity reactor. Nitrogen oxide was the mixture of NO and $NO_2$ in a molar ratio of 4:1, and the molar ratio of NO to oxygen was 4:1. Under the conditions including a reaction temperature of 100° C., a reaction pressure of 0.8 MPa, a butanol/NO molar ratio of 3:1, and a rotating speed of the rotor in the rotating high-gravity reactor of 2,000 rpm, the raw materials were contacted and reacted in the rotating high-gravity reactor, and the results showed that the selectivity of butyl nitrite was 99.18%.

Example 7

005CR type resin catalyst (Jiangsu Suqing Water Treatment Engineering Group Co., Ltd.) labelled as Suqing brand was loaded into the high-gravity reactor. Nitrogen oxide, oxygen and propanol were fed in a cross current manner into the rotating high-gravity reactor. Nitrogen oxide was the mixture of NO and $NO_2$ in a molar ratio of 3:1, and the molar ratio of NO to oxygen was 4:1. Under the conditions including a reaction temperature of 40° C., a reaction pressure of 0.05 MPa, a propanol/NO molar ratio of 10:1, and a rotating speed of the rotor in the rotating high-gravity reactor of 1,000 rpm, the raw materials were contacted and reacted in the rotating high-gravity reactor, and the results showed that the selectivity of propyl nitrite was 99.91%.

Example 8

Nitrogen oxide, oxygen and ethanol were fed in a counter current manner into the rotating high-gravity reactor. Nitrogen oxide was NO, and the molar ratio of NO to oxygen was 4.5:1. Under the conditions including a reaction temperature of 40° C., a reaction pressure of 0.05 MPa, an ethanol/NO molar ratio of 1.2:1, and a rotating speed of the rotor in the rotating high-gravity reactor of 4,000 rpm, the raw materials were contacted and reacted in the rotating high-gravity reactor, and the results showed that the selectivity of ethyl nitrite was 99.68%.

Example 9

Nitrogen oxide, oxygen and methanol were fed in a counter current manner into the rotating high-gravity reactor. Nitrogen oxide was the mixture of NO and $NO_2$ in a molar ratio of 2:1, and the molar ratio of NO to oxygen was 10:1. Under the conditions including a reaction temperature of 50° C., a reaction pressure of 0.2 MPa, a methanol/NO molar ratio of 1.5:1, and a rotating speed of the rotor in the rotating high-gravity reactor of 3,000 rpm, the raw materials were contacted and reacted in the rotating high-gravity reactor, and the results showed that the selectivity of methyl nitrite was 99.87%.

Example 10

D002 type resin catalyst (Jiangsu Suqing Water Treatment Engineering Group Co., Ltd.) labelled as Suqing brand was loaded into the high-gravity reactor. Nitrogen oxide, oxygen and methanol were fed in a counter current manner into the rotating high-gravity reactor. Nitrogen oxide was the mixture of NO and $NO_2$ in a molar ratio of 2:1, and the molar ratio of NO to oxygen was 20:1. Under the conditions including a reaction temperature of 30° C., a reaction pressure of 0.06 MPa, a methanol/NO molar ratio of 10:1, and a rotating speed of the rotor in the rotating high-gravity reactor of 1,800 rpm, the raw materials were contacted and reacted in the rotating high-gravity reactor, and the results showed that the selectivity of methyl nitrite was 99.85%.

Example 11

Nitrogen oxide, oxygen and methanol were fed in a counter current manner into the rotating high-gravity reactor. Nitrogen oxide was NO, and the molar ratio of NO to oxygen was 4.5:1. Under the conditions including a reaction temperature of 5° C., a reaction pressure of −0.02 MPa, a methanol/NO molar ratio of 1.5:1, and a rotating speed of the rotor in the rotating high-gravity reactor of 800 rpm, the raw materials were contacted and reacted in the rotating high-gravity reactor, and the results showed that the selectivity of methyl nitrite was 99.49%.

Example 12

D002-II type resin catalyst (Jiangsu Suqing Water Treatment Engineering Group Co., Ltd.) labelled as Suqing brand was loaded into the high-gravity reactor. Nitrogen oxide, oxygen and methanol were fed in a counter current manner into the rotating high-gravity reactor. Nitrogen oxide was NO, and the molar ratio of NO to oxygen was 5:1. Under the conditions including a reaction temperature of 40° C., a reaction pressure of 0.01 MPa, a methanol/NO molar ratio of 1.5:1, and a rotating speed of the rotor in the rotating high-gravity reactor of 2,500 rpm, the raw materials were contacted and reacted in the rotating high-gravity reactor, and the results showed that the selectivity of methyl nitrite was 99.83%.

Example 13

The conditions and reaction materials were the same as those in Example 12, except for using a fixed bed reactor (having the model of FBR25-800 and manufactured by Shanghai Research Institute of Petrochemical Technology). The selectivity of methyl nitrite was 99.11%.

Comparative Example 1

The conditions and reaction materials were the same as those in Example 1, except for using a fixed bed reactor (having the model of FBR25-800 and manufactured by Shanghai Research Institute of Petrochemical Technology). The selectivity of methyl nitrite was 98.05%.

The technological conditions and results thereof in the aforesaid examples are generalized in the following Table 1.

TABLE 1

| Example No. | Catalyst | Reactor | Reaction temperature, ° C. | Reaction pressure, MPa | $NO:O_2$ (molar ratio) | Alcohol:NO (molar ratio) | Selectivity of nitrite, % |
|---|---|---|---|---|---|---|---|
| Exp. 1 | None | Rotating high-gravity reactor (having a rotating speed of 1000 rpm) | 40 | 0.2 | 10:1 | 1.5:1 | 99.67 |

TABLE 1-continued

| Example No. | Catalyst | Reactor | Reaction temperature, °C. | Reaction pressure, MPa | $NO:O_2$ (molar ratio) | Alcohol:NO (molar ratio) | Selectivity of nitrite, % |
|---|---|---|---|---|---|---|---|
| Exp. 2 | None | Rotating high-gravity reactor (having a rotating speed of 500 rpm) | 10 | −0.08 | 6:1 | 2:1 | 99.25 |
| Exp. 3 | 002CR | Rotating high-gravity reactor (having a rotating speed of 1200 rpm) | 30 | −0.05 | 1.5:1 | 1.5:1 | 99.71 |
| Exp. 4 | None | Rotating high-gravity reactor (having a rotating speed of 3000 rpm) | 50 | −0.02 | 8:1 | 20:1 | 99.43 |
| Exp. 5 | 005CR | Rotating high-gravity reactor (having a rotating speed of 1500 rpm) | 30 | 0.2 | 20:1 | 5:1 | 99.88 |
| Exp. 6 | None | Rotating high-gravity reactor (having a rotating speed of 2000 rpm) | 100 | 0.8 | 4:1 | 3:1 | 99.18 |
| Exp. 7 | 005CR | Rotating high-gravity reactor (having a rotating speed of 1000 rpm) | 40 | 0.05 | 4:1 | 10:1 | 99.91 |
| Exp. 8 | None | Rotating high-gravity reactor (having a rotating speed of 4000 rpm) | 40 | 0.05 | 4.5:1 | 1.2:1 | 99.68 |
| Exp. 9 | None | Rotating high-gravity reactor (having a rotating speed of 3000 rpm) | 50 | 0.2 | 10:1 | 1.5:1 | 99.87 |
| Exp. 10 | D002 | Rotating high-gravity reactor (having a rotating speed of 1800 rpm) | 30 | 0.06 | 20:1 | 10:1 | 99.85 |
| Exp. 11 | None | Rotating high-gravity reactor (having a rotating speed of 800 rpm) | 5 | −0.02 | 4.5:1 | 1.5:1 | 99.49 |
| Exp. 12 | D002-II | Rotating high-gravity reactor (having a rotating speed of 2500 rpm) | 40 | 0.01 | 5:1 | 1.5:1 | 99.83 |
| Exp. 13 | D002-II | Fixed bed | 40 | 0.01 | 5:1 | 1.5:1 | 99.11 |
| Com. Exp. 1 | None | Fixed bed | 40 | 0.2 | 10:1 | 1.5:1 | 98.05 |

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A process for producing $C_1$-$C_4$ alkyl nitrite, comprising: loading a porous filler layer into a reactor;
passing nitrogen oxide, oxygen and an alkanol chosen from $C_1$-$C_4$ alkanol through the porous filler layer in a counter current, parallel current or cross current manner,
wherein the reactor has a reaction temperature ranges from 0 to 150° C., a reaction pressure ranges from −0.09 to 1.5 MPa, a molar ratio of $C_1$-$C_4$ alkanol to nitrogen oxide ranges from 1-100:1, and a molar ratio of nitrogen oxide to oxygen ranges from 4-50:1,
wherein said nitrogen oxide is NO, or a mixed gas containing NO and one or more selected from $N_2O_3$ and $NO_2$,
wherein the reactor is a rotating high-gravity reactor comprising a rotor.

2. The process for producing $C_1$-$C_4$ alkyl nitrite according to claim 1, characterized in that the porous filler layer is fixed onto the rotor.

3. The process for producing $C_1$-$C_4$ alkyl nitrite according to claim 2, wherein the reactor further comprises a resin catalyst fixed onto the rotor.

4. The process for producing $C_1$-$C_4$ alkyl nitrite according to claim 3, characterized in that the resin catalyst is an acidic ion exchange resin catalyst.

5. The process for producing $C_1$-$C_4$ alkyl nitrite according to claim 1, characterized in that the molar number of NO in the nitrogen oxide is greater than that of $NO_2$, if any, in the nitrogen oxide.

6. The process for producing $C_1$-$C_4$ alkyl nitrite according to claim 1, characterized in that the reaction temperature ranges from 10 to 100° C.; the reaction pressure ranges from −0.05 to 1.0 MPa; the molar ratio of $C_1$-$C_4$ alkanol to nitrogen oxide is 1-50:1; and the molar ratio of nitrogen oxide to oxygen is 4-20:1.

7. The process for producing $C_1$-$C_4$ alkyl nitrite according to claim 6, characterized in that the reaction temperature ranges from 10 to 60° C.; the reaction pressure ranges from −0.05 to 0.8 MPa; the molar ratio of $C_1$-$C_4$ alkanol to nitrogen oxide is 1-20:1; and the molar ratio of nitrogen oxide to oxygen is 4-10:1.

8. The process for producing $C_1$-$C_4$ alkyl nitrite according to claim 1, characterized in that the rotor in the rotating high-gravity reactor has a rotating speed of from 100 to 5,000 rpm.

9. The process for producing $C_1$-$C_4$ alkyl nitrite according to claim 8, characterized in that the rotor in the rotating high-gravity reactor has a rotating speed of from 300 to 3,000 rpm.

10. The process for producing $C_1$-$C_4$ alkyl nitrite according to claim 1, characterized in that the alkanol is selected from the group consisting of methanol, ethanol and n-propanol.

11. The process for producing $C_1$-$C_4$ alkyl nitrite according to claim 10, characterized in that the alkanol is methanol or ethanol.

12. The process for producing $C_1$-$C_4$ alkyl nitrite according to claim 1, characterized in that the porous filler layer comprises an inert filler web, a porous web, a stent or a porous plate.

13. A process for producing $C_1$-$C_4$ alkyl nitrite, comprising:
loading a resin catalyst into a reactor;
passing nitrogen oxide, oxygen and an alkanol chosen from $C_1$-$C_4$ alkanols through the resin catalyst in a counter current, parallel current or cross current manner,
wherein a reaction temperature ranges from 0 to 150° C., a reaction pressure ranges from −0.09 to 1.5 MPa, a molar ratio of $C_1$-$C_4$ alkanol to nitrogen oxide ranges from 1-100:1, and a molar ratio of nitrogen oxide to oxygen ranges from 4-50:1,
wherein said nitrogen oxide is NO, or a mixed gas containing NO and one or more selected from $N_2O_3$ and $NO_2$.

14. The process for producing $C_1$-$C_4$ alkyl nitrite according to claim 13, wherein the reactor is a fixed bed reactor or a rotating high-gravity reactor.

15. The process for producing $C_1$-$C_4$ alkyl nitrite according to claim 13, wherein the reactor is a rotating high-gravity reactor and the resin catalyst is fixed onto a rotor of the rotating high-gravity reactor.

16. The process for producing $C_1$-$C_4$ alkyl nitrite according to claim 13, wherein the reaction temperature ranges from 10 to 100° C., the reaction pressure ranges from −0.05 to 1.0 MPa, the molar ratio of $C_1$-$C_4$ alkanol to nitrogen oxide is 1-50:1, and the molar ratio of nitrogen oxide to oxygen is 4-20:1.

17. The process for producing $C_1$-$C_4$ alkyl nitrite according to claim 16, characterized in that the reaction temperature ranges from 10 to 60° C., the reaction pressure ranges from −0.05 to 0.8 MPa, the molar ratio of $C_1$-$C_4$ alkanol to nitrogen oxide is 1-20:1, and the molar ratio of nitrogen oxide to oxygen is 4-10:1.

18. The process for producing $C_1$-$C_4$ alkyl nitrite according to claim 15, characterized in that the rotor in the rotating high-gravity reactor has a rotating speed of from 100 to 5,000 rpm.

19. The process for producing $C_1$-$C_4$ alkyl nitrite according to claim 18, characterized in that the rotor in the rotating high-gravity reactor has a rotating speed of from 300 to 3,000 rpm.

* * * * *